United States Patent [19]
Savage et al.

[11] Patent Number: 5,882,602
[45] Date of Patent: Mar. 16, 1999

[54] INTEGRAL FLUID AND WASTE CONTAINER FOR BLOOD ANALYZER

[75] Inventors: Douglas R. Savage, Del Mar; Michael C. Weinzierl, San Diego, both of Calif.

[73] Assignee: SenDx Medical, Inc., Carlsbad, Calif.

[21] Appl. No.: 815,425

[22] Filed: Mar. 11, 1997

Related U.S. Application Data

[62] Division of Ser. No. 650,340, May 20, 1996.

[51] Int. Cl.⁶ .................. F16L 37/28; B01L 3/00
[52] U.S. Cl. .................. 422/103; 422/63; 422/81; 422/102; 422/104; 436/43; 436/180; 137/614.03; 137/614.05; 251/149.6; 251/149.7
[58] Field of Search .................. 422/102, 63, 100, 422/103, 104; 436/43, 174, 180; 222/94, 95, 132, 325; 220/403, 404; 137/614.03, 604.05, 6; 251/149.6, 902, 149.7

[56] References Cited

U.S. PATENT DOCUMENTS

| | | | |
|---|---|---|---|
| 3,874,850 | 4/1975 | Sorensen, et al. | 23/230 |
| 4,003,705 | 1/1977 | Buzza et al. | 23/230 |
| 4,116,336 | 9/1978 | Sorensen et al. | 206/524.8 |
| 4,415,085 | 11/1983 | Clarke et al. | 206/526 |
| 4,445,539 | 5/1984 | Credle | 137/614.03 |
| 4,588,554 | 5/1986 | Kaartinen et al. | 422/61 |
| 4,649,028 | 3/1987 | Kaltenbach et al. | 422/100 |
| 4,786,394 | 11/1988 | Enzer et al. | 204/401 |
| 4,869,398 | 9/1989 | Colvin et al. | 222/83 |
| 4,871,439 | 10/1989 | Enzer et al. | 204/401 |
| 5,031,797 | 7/1991 | Boris et al. | 222/23 |
| 5,084,158 | 1/1992 | Inoue | 204/411 |
| 5,163,900 | 11/1992 | Wortrich | 604/30 |
| 5,230,427 | 7/1993 | Betts et al. | 206/213.1 |
| 5,279,797 | 1/1994 | Burns et al. | 422/102 |
| 5,477,883 | 12/1995 | Totten | 137/614.03 |
| 5,484,428 | 1/1996 | Drainville et al. | 604/319 |
| 5,540,265 | 7/1996 | Polaschegg et al. | 141/301 |
| 5,555,908 | 9/1996 | Edwards et al. | 137/329.1 |
| 5,665,315 | 9/1997 | Robert et al. | 422/102 |

FOREIGN PATENT DOCUMENTS 2 100 859 A   1/1983   United Kingdom.

*Primary Examiner*—Long V. Le
*Attorney, Agent, or Firm*—Fish & Richardson P.C.

[57] ABSTRACT

A calibration fluid cartridge for a medical device, such as a blood analyzer. The cartridge includes at least one calibrant bag that is filled with a flexible calibration fluid and a flexible waste bag for holding fluid waste from the blood analyzer. The calibrant bags contract as calibration fluid exits the bags, leaving a void in the cartridge that is filled by the waste bag, which expands with waste fluids as the calibrant bags contract. Thus, the cartridge can be made compact and light-weight, making it particularly suited for use in a portable blood analyzer. The calibrant bags have fluid ports with self-sealing valves and a flange to secure them within the cartridge, as well as a compliant member for facilitating a secure, fluid-tight seal between fluid fitting on the blood analyzer and the calibrant and waste bags. The calibrant bags can be directly coupled to the blood analyzer to reduce diffusion of gases from the calibrant bags.

21 Claims, 10 Drawing Sheets

INTEGRAL FLUID AND WASTE CONTAINER FOR BLOOD ANALYZER

RELATED APPLICATIONS

This is a divisional of copending application Ser. No. 08/650,340, filed May 20, 1996.

This application is related to co-pending U.S. patent application Ser. No. 08/650,624, entitled "Waste Container for Portable Blood Analyzer;" U.S. patent application Ser. No. 08/650,341, entitled "Portable Modular Blood Analyzer with Simplified Fluid Handling Sequence;" U.S. patent application Ser. No. 08/650,622, entitled "Blood Gas/Electrolyte Calibrator and Method for Use;" U.S. patent application Ser. No. 08/650,465, entitled "Reference Solution Container for Blood Gas/Electrolyte Measuring System;" U.S. patent application Ser. No. 08/648,692, entitled "Locking Sensor Cartridge with Integral Fluid Port, Electrical Connections, and Pump Tube; U.S. patent application Ser. No. 08/649,009, entitled "Sensors with Subminiature Through Holes and Method for Fabricating Such Sensors;" U.S. patent application Ser. No. 08/648,675, entitled "Electronic Wiring Substrate with Subminiature Through Holes and Method for Fabricating Such Sensors;" U.S. patent application Ser. No. 08/648,676, entitled "A Sensor Cartridge for an Analyte Analyzer;" U.S. patent application Ser. No. 08/648,694, entitled "Method and Apparatus for Drilling Subminiature Through Holes in a Sensor Substrate;" and U.S. patent application Ser. No. 08/649,525, entitled "Method and Apparatus for Ratiometric Measurement of Hematocrit," which are all assigned to the assignee of the present invention.

BACKGROUND OF THE INVENTION

1. Field of the Invention

This invention relates to an apparatus for storing calibration and waste fluids for medical devices. More particularly, the present invention relates to a calibration fluid cartridge, including a calibrant fluid container and a waste fluid container, for use in a blood analyzer and other medical devices for analyzing bodily fluids.

2. Description of Related Art

Blood analysis machines and other medical devices require reference solutions to periodically calibrate the system to optimize analytical performance. (For convenience, the remainder of this description will refer to blood analysis machines. It should be understood, however, that such machines are only exemplary and that the present invention can be applied to any type of medical fluid analysis device, such as for urine, spinal fluid, semen, and other bodily fluids.) In such devices, a method of waste collection is required to safely store the expended calibration fluid and potentially hazardous blood (or other fluid) samples. Thus, such devices include containers to hold the calibration fluids as well as waste containers to hold the expended calibration fluid and blood samples.

Many conventional blood analysis machines package the calibration and waste fluids in rigid containers that are attached to the blood analysis machine. Because these containers are rigid, they occupy a great deal of space on the blood analysis machine. Moreover, the rigid containers are expensive and heavy. Other conventional blood analysis machines package the calibration fluid separately and collect the waste fluids into a disposable container via the force of gravity on the waste fluids. These systems are highly complex for the users, as the components require individual monitoring and disposal.

Still other conventional blood analysis machines package the sensor element, calibrant, and waste fluids in individual test cartridges. While this system is user friendly to a certain extent, it is very cost prohibitive, as individual test cartridges must be purchased for every blood sample.

In addition, some blood analysis machines are only concerned with the analysis of electrolytes, rather than gases and electrolytes, and therefore do not require gas tight sealing between a main device housing and the cartridge holding the calibration and waste fluid containers. An example of such a blood analysis machine is disclosed in U.S. Pat. No. 4,649,028, where the cartridge has calibration and waste fluid containers connected to the main housing by a connector and tubing that are gas permeable. Furthermore, a pump is required to pull the calibration fluid from the calibrant bag, because access to the fluids in the bag is by a port on the top of the bag.

Therefore, a need exists for a calibration and waste fluid collection container for use in a blood analysis machine or other medical fluid analysis device, in which the calibration fluids and waste collection container are packaged into a gas tight, user friendly, cost effective, efficient, accurate package. The present invention provides such a calibration and waste fluid collection container.

SUMMARY OF THE INVENTION

The details of the preferred embodiment of the present invention are set forth in the accompanying drawings and the description below. Once the details of the invention are known, numerous additional innovations and changes will become obvious to one skilled in the art.

The present invention is a cartridge for holding calibration and waste fluids in a blood analysis machine or other medical device. Preferably, the container is designed for use in a portable blood analyzer, where it is important that the cartridge be light-weight, compact, and inexpensive. Further, because calibrant fluids may contain gases held in solution, it is important for the cartridge to make a substantially gas-tight connection when installed on the blood analysis machine. (For convenience, the remainder of this description shall refer to the medical device in which the present invention is used as a "blood analyzer." Moreover, for convenience, the remainder of this description shall refer to the apparatus that holds the calibration fluid and waste containers as a "cartridge." It should be recognized, however, that this term is not intended to be limiting on the structure of the present invention, but rather is merely used as a convenience.)

In the present invention, both the calibration and waste fluids are preferably provided in a single cartridge or container. The cartridge can be secured within a main housing of the blood analysis machine via rails on the cartridge that mate to grooves on the main housing, in order to guide the cartridge into the blood analyzer housing. Preferably, the cartridge has a latch that securely locks the cartridge in place within the housing. The mating connection between fluid fittings on the blood analyzer and the cartridge is substantially gas-tight.

The cartridge of the present invention includes at least one flexible calibrant bag for holding a calibration fluid. Preferably, the cartridge includes at least two flexible calibrant bags. The cartridge of the present invention also includes at least one flexible waste bag for holding waste fluid from the blood analyzer. The flexible calibrant bag contracts as calibration fluid exits the calibrant bag, thereby creating a void within the cartridge. The flexible waste bag expands to substantially fill this void.

Each calibrant bag includes a fluid communication port. The cartridge has a calibration bag locating element corresponding to each port. The fluid communication port includes a port body that has a fluid communication path extending throughout the length of the port body. The port body, at one end, is preferably a female receptacle that accepts a male flow fitting (preferably a Luer fitting) on the blood analysis machine that allows calibration fluid to flow through the port body. The other end of the port body engages the calibrant bag, and the port body and calibrant bag are preferably heat sealed together. Alternatively, the calibrant bag and the port body can be adhesively secured to one another. The fluid communication port of a calibration bag also includes a self-sealing valve, which is located substantially within the fluid communication path, that prevents the flow of calibration fluid through the port body, unless the flow fitting (e.g., the Luer fitting) is engaging the self-sealing valve. Finally, the fluid communication port includes a flange that is coupled to the port body for securing the fluid communication port to the locating element on the cartridge. Preferably, the flange and port body are an integral unit from the polyolefin family of plastics. Moreover, the self-sealing valve is preferably a poppet valve that has a valve stem and a stem backstop that fit within the port body.

Each flexible calibrant bag contained within the cartridge may have a protective covering. In a preferred embodiment of the present invention, the flexible calibrant bags are made from an aluminum material, such as an aluminum laminate foil, that is heat sealed around its perimeter. Because the cartridge of the present invention is preferably used in portable blood analyzers, the flexible aluminum calibrant bags are subject to the formation of pin holes while the filled calibrant bags are being shipped to a medical facility or are being moved around in a medical facility. In addition, the cartridge is subject to significant vibrations, which may result in damage to the flexible aluminum calibrant bags. Thus, a flexible protective layer may be applied such that it covers a substantial portion of the exterior surface of the flexible calibrant bag.

A flexible protective layer may be applied to the flexible aluminum calibrant bags in the following manner. First, the flexible bag is formed from the aluminum material. Then, the flexible protective layer is applied to cover a substantial portion of the exterior surface of the flexible calibrant bag. Preferably, the flexible protective layer is applied to the exterior of the flexible bag before the bag is filled with calibration fluid.

Because the cartridge of the present invention has several fluid communication ports, one each corresponding to each of the flexible calibrant bags and flexible waste bags, the cartridge of the present invention is preferably designed such that there is tolerance between the fluid communication ports of the cartridge and the flow fittings of the blood analyzer. In this respect, the cartridge is supplied with resilient members (preferably leaf springs) that allow each fluid port to be substantially equally engaged by the corresponding flow fitting of the blood analyzer. This arrangement accounts for the possibility that the flow fittings of the blood analyzer may be of different lengths, or there may be some misalignment between the flow fittings and the fluid communication ports of the cartridge. With the compliant fluid communication ports of the present invention, there is sufficient tolerance to allow each port and fitting to be substantially equally engaged, with a substantially gas-tight fit, when the cartridge is positioned with in the blood analyzer.

The details of the preferred embodiment in the present invention are set forth in the accompanying drawings and the description below. Once the details of the invention are known, numerous additional innovations and modifications will become obvious to one skilled in the art.

DETAILED DESCRIPTION OF THE INVENTION

Throughout this description, the preferred embodiment and examples shown should be considered as exemplars, rather than as limitations on the present invention.

I. Overview

Figure 1:
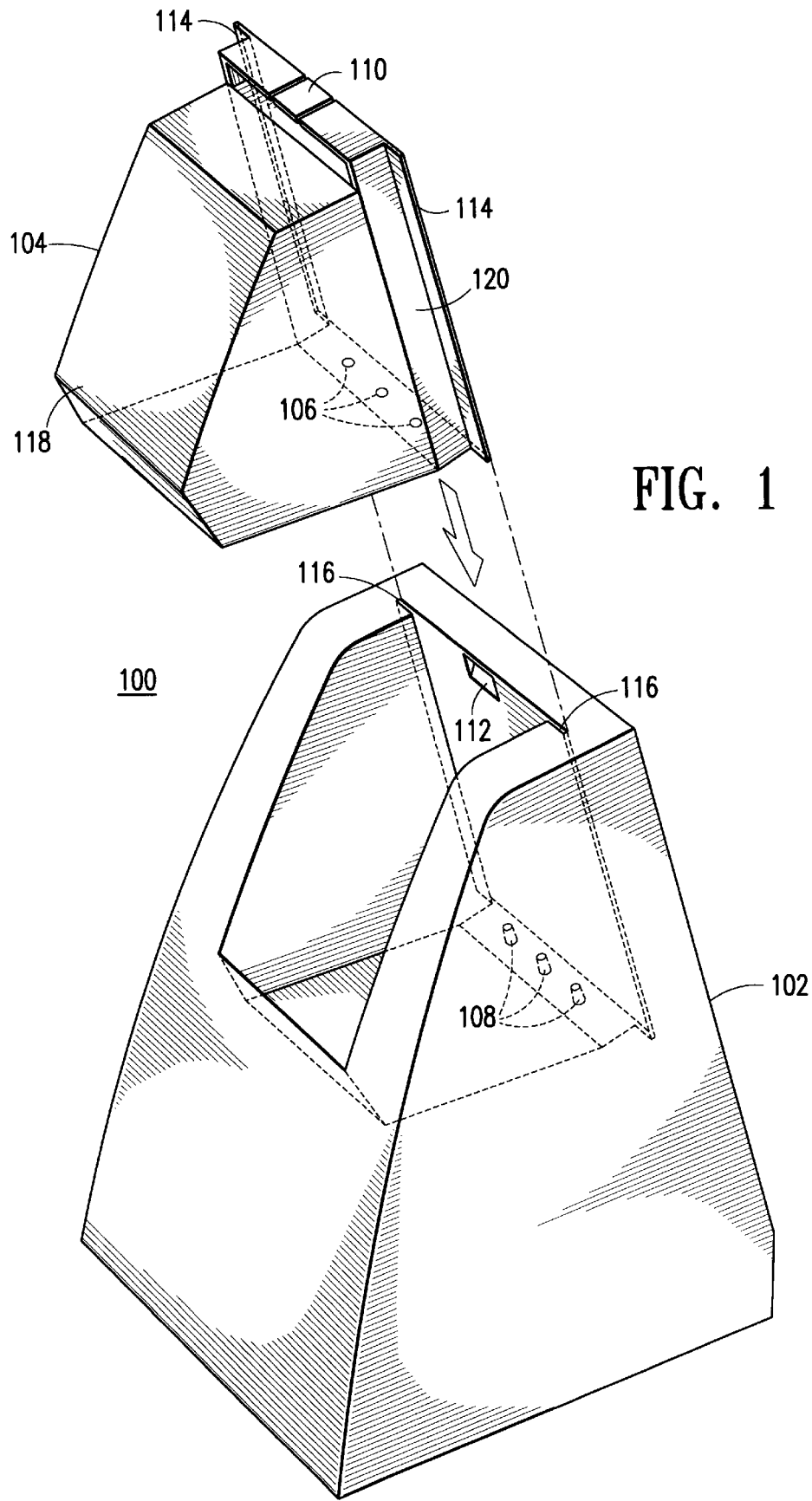
FIG. 1 is a perspective view of a blood analyzer, showing the main housing of the analyzer and the cartridge for holding calibrant and waste containers.

FIG. 1 is a perspective view of a blood analyzer 100, showing the main housing 102 of the analyzer and the cartridge 104 for holding calibrant and waste containers. The blood analyzer 100 is preferably a portable unit that can be taken from patient to patient to perform blood tests, rather than requiring patients' blood samples to be taken to a laboratory in which a non-portable analyzer is located. As can be seen, the cartridge 104 can be removed from the main housing 102 and can therefore be replaced, repaired, or modified, as necessary.

The cartridge 104 has a plurality of fitting holes 106 (as shown, three) that permit the passage of fluids between the housing 102 and the calibrant and waste containers (not shown) within the cartridge 104. Thus, the housing has a plurality of fluid fittings 108, corresponding in number to the fitting holes 106, that mate to fluid ports (not shown) of the cartridge 104 when it is inserted fully into the housing 102. As shown, the fluid fittings 108 are preferably a male-type fitting that fit within and through the fitting holes 106.

The cartridge 104 and housing 102 have latching mechanisms 110, 112 that engage when the cartridge 104 is inserted into the housing 102, fastening the two together. Preferably, the cartridge has a pivoting or flexing latch 110 that falls into a notch 112 on the housing 102. The mating latching mechanism 110, 112 locks the cartridge 104 within the housing 102 to ensure that the fluid ports and fluid fittings 108 remain engaged (i.e., remain in fluid communication) and are not dislodged due to jarring, vibration, or other motion of the analyzer 100. Those skilled in the art will appreciate that the cartridge 104 and housing 102 may be fastened together by any type of latching or locking mechanism (e.g., magnetic) and that the latching mechanism illustrated in FIG. 1 is merely exemplary.

Figure 8:
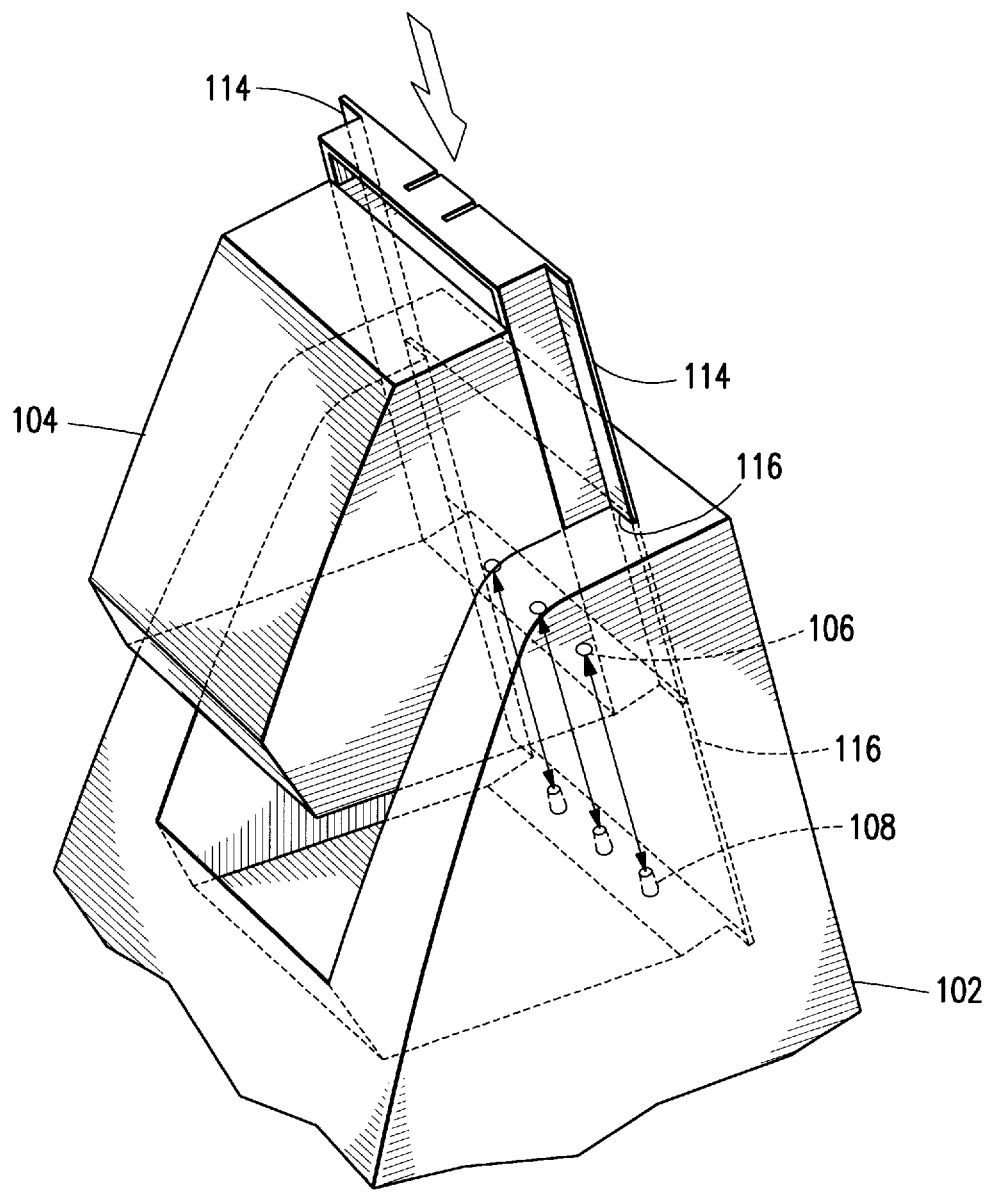
FIG. 8 shows a cartridge being inserted into the housing.

The cartridge 104 has rails 114 corresponding to grooves 116 formed in the housing 102. As the cartridge 104 is inserted into the housing 102, the rails 114 and grooves 116 engage to ensure that the cartridge 104 is properly aligned within the housing 102. This feature facilitates engagement of the fluid ports and fluid fittings 108 as the cartridge 104 is inserted into the housing 102. Of course, many other means exist for aligning the cartridge 104 within the housing 102; the rails 114 and grooves 116 are merely exemplary. FIG. 8 shows the cartridge 104 being inserted into the housing 102, illustrating how the rails 114 fit within the grooves 116 and how the fluid fittings 108 are mated to the fitting holes 106.

The exemplary cartridge 104 illustrated in FIG. 1 has a side tray 120 and a cover 118. The side tray 120 has the fitting holes 106 formed in it. The cover 118 protects the calibrant and waste containers within the cartridge 104 and makes the cartridge 104 self-contained and simple to use. It should be understood, however, that the configuration and structural features of the cartridge 104 (including the side tray 120, cover 118, and positioning of the fitting holes 106) shown in FIG. 1 is merely exemplary. Many different configurations could be devised. Moreover, the cartridge need not completely cover the fluid containers and need not have rails 114.

II. Cartridge Structure

Figure 2:
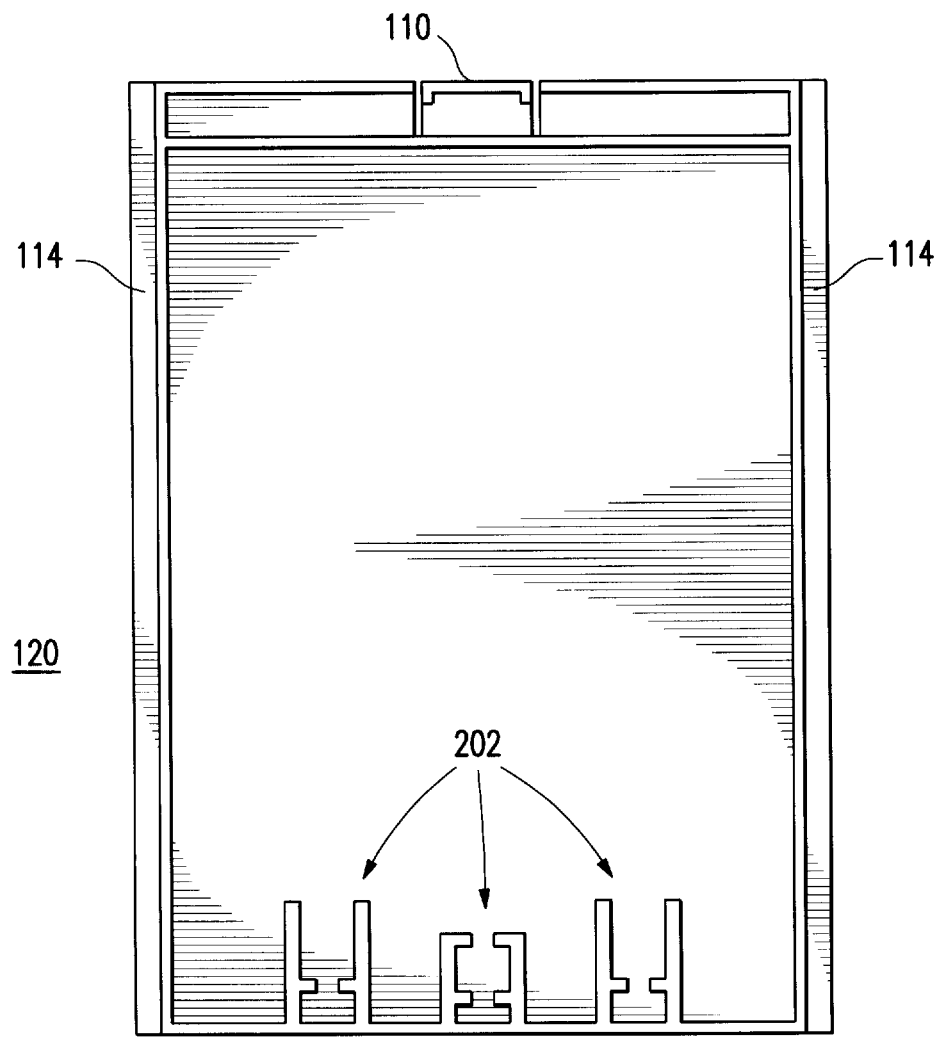
FIG. 2 is a top view of the cartridge side plate without the calibrant and waste containers.

FIG. 2 is a top view of the side tray 120 without the calibrant and waste containers. This view shows the rails 114 and latch 110. In addition, this view shows the walls 202 that hold the fluid communication ports (not shown) of the calibrant and waste containers.

Figure 3:
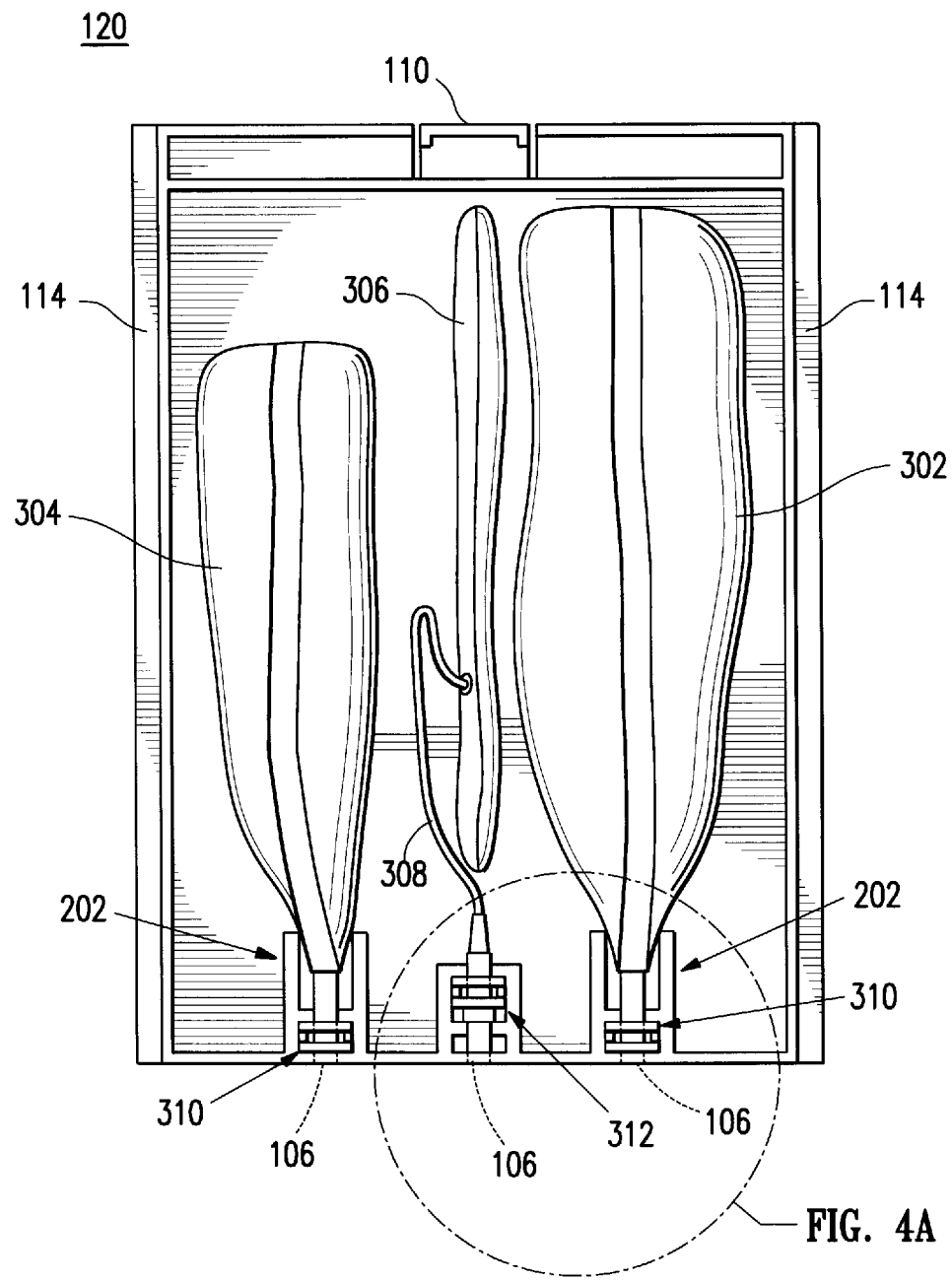
FIG. 3 shows the side plate with the calibrant containers and waste container in place.

FIG. 3 shows the side tray 120 with the calibrant containers 302, 304 and waste container 306 in place. As shown, the calibrant containers 302, 304 are full, and the waste container 306 is empty. Preferably, both the calibrant containers 302, 304 and the waste container 306 are flexible bags that expand and contract as fluid enters and exits the bags, respectively.

FIG. 3 shows two calibrant bags 302, 304 and one waste bag 306 in the side tray 120. It should be understood, however, that such an arrangement is merely exemplary and that the cartridge 104 could contain fewer or more than two calibrant bags and more than one waste bag. There is some advantage, however, to having at least two calibrant bags 302, 304. The first calibrant bag 302 may have approximately twice the volume of the second bag 304, so that the first bag can be used for periodically calibrating the blood analyzer 100 as well as for flushing the analyzer 100 after each blood sample is tested. The other, smaller calibrant bag 304 can then be used strictly for calibration.

Making both the calibrant bags 302, 304 and waste bag 306 flexible, as opposed to rigid, allows the cartridge 104 to be made more compact and thus lighter than it would be with inflexible fluid containers. As blood samples are processed by the blood analyzer 100, calibration fluid in the calibrant bags 302, 304 is used to calibrate and flush the analyzer 100. This results in a depletion of calibrant fluid in the calibrant bags 302, 304, which, because they are flexible, decrease in volume. At the same time, the waste bag 306 is being filled with waste fluids (i.e., processed blood and calibration fluid from flushing and calibrating the analyzer 100), causing the flexible waste bag 306 to expand or increase in volume. Thus, while the calibrant bags 304, 306 are decreasing in volume, leaving a void within the cartridge 104, the waste bag 306 is expanding to fill the void left in the cartridge 104 by the emptying calibrant bags 304, 306. Consequently, the physical size and the weight of the cartridge 104 is reduced. This is particularly advantageous in portable blood analyzers, which must be lightweight and compact.

FIG. 3 also shows the fluid communication port 310 for the calibration bags 302, 304 as well as the fluid communication port 312 for the waste bag 306. The fluid communication ports 310, 312 are coupled to the calibrant bags 302, 304 and the waste bag 306, respectively, which in turn can be coupled to the fluid fittings 108 of the main housing 102. These ports 310, 312 allow fluid communication between the main housing 102 and the cartridge 104. The waste bag is preferably coupled to fluid communication port 312 by a length of plastic tubing 308, while the calibrant bags 302, 304 are preferably directly coupled to ports 310.

Directly coupling the calibrant bags 302, 304 to the fluid communication ports 310 permits the connection between the calibrant bags 302, 304 and main housing 102 to be substantially gas tight. This allows the cartridge 104 of the present invention to be used with blood analyzers that analyze gases and electrolytes present in blood. The connections between the calibrant bags 302, 304 and main housing 102 as well as between the bag 306 and housing 102 also prevent any appreciable leak of fluids. This is important in a portable blood analyzer, which is susceptible to fluid spills when it is being moved around.

To facilitate a substantially gas-tight/fluid-tight connection between the calibrant bags 302, 304 and the housing 102, walls 202 are formed on the cartridge 104, so that the calibrant bags 302, 304 can be directly coupled to the fluid fittings on the housing 102. Direct coupling eliminates the need for flexible tubing connecting the bags 302, 304 to the fitting 108 and thereby substantially eliminates the escape of gases through such tubing.

III. Fluid Communication Ports

Figure 4A:
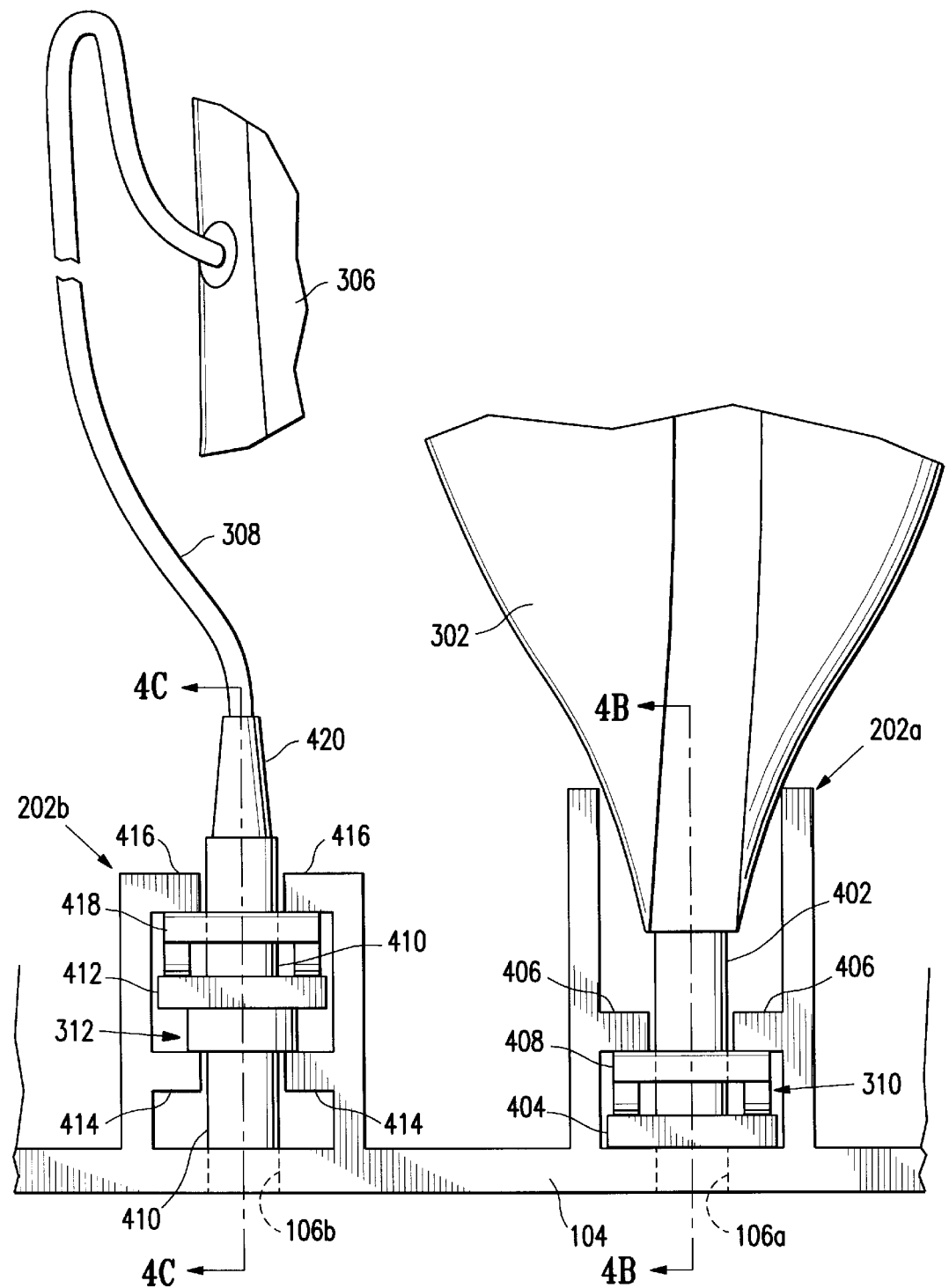
FIGS. 4A–4C are exploded views of the side plate of FIG. 3 showing the exemplary fluid communication ports of the cartridge.

FIG. 4A is an exploded view from FIG. 3 showing the exemplary fluid communication ports 310, 312 of the cartridge 104. With respect to the preferred fluid communication port 310 for the exemplary calibrant bag 302, the calibrant port 310 corresponds to a fitting hole 106a and includes walls 202a, which hold the calibrant bag 302 and the calibrant port 310 in place within the cartridge 104. The calibrant fluid communication port 310 includes a port body 402 and a flange 404. The flange 404 secures the calibrant port 310 within the walls 202a by means of calibrant port retaining walls 406. The flange 404 and port body 402 may be integral and formed from a plastic material, such as polypropylene. Those skilled in the art will recognize that other suitable materials exist for the port body 402.

Preferably, the port 310 includes a compliant member 408 to provide tolerance between the calibrant port 310 and the fluid fitting 108. As shown, the compliant member 408 is a leaf spring (preferably, beryllium-copper) that is seated between the flange 404 and the retaining walls 406. Thus, as a fluid fitting 108 engages the calibrant port 310, the compliant member 408 provides some tolerance (preferably, +/−20/1000") between the port 310 and the fitting 108. Those skilled in the art will recognize, however, that the fluid communication port assembly for the calibrant bag 302 shown in FIG. 4A (including the compliant member 408) is merely exemplary. It is preferable to have some tolerance between the fluid fitting 108 and the calibrant port 310 to ensure substantially gas and fluid tight engagement between all communication ports 310, 312 on the cartridge 104 and all fittings 108, but tolerance can be attained in a variety of ways, such as by a coil spring, rubber member, or hydraulic means, as those skilled in the art will appreciate.

The waste bag fluid communication port 312 corresponds to another fitting hole 106b and includes walls 202b, which maintain the waste port 312 in place within the cartridge 104. The waste port 312 includes a port body 410 and a flange 412. The flange 412 is disposed between front retaining walls 414 and rear retaining walls 416 and maintains the waste port 312 within the walls 202b by means of the front and rear retaining walls 414, 416. Again, as with the calibrant port 310, a compliant member 418 is preferably employed to provide tolerance between the waste port 312 and the corresponding fluid fitting 108. Again, the compliant member 418 is preferably a leaf spring, but any means of providing tolerance can be employed. A shock relieving sleeve 420 can be employed to secure the tubing 308 to the waste port 312.

Figure 4B:
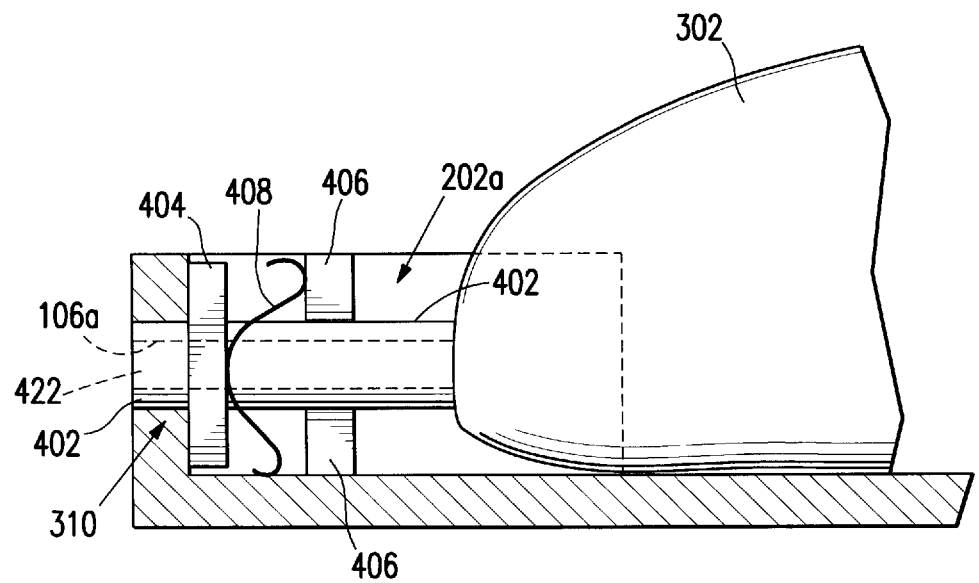

FIG. 4B is a cross-sectional view of the calibrant fluid communication port 310. The retaining wall 406 holds the leaf spring 408 in place, which in turn provides a back-stop for the flange 404. When a fluid fitting 108 engages the calibrant port 310, the port 310 is forced rightward (with reference to FIG. 4B), and the flange 404 is forced against the leaf spring 408. The leaf spring 408 provides compliance against the force of the fluid fitting 108, but also forces the calibrant port 310 leftward back against the fluid fitting 108 to ensure proper engagement of the fitting 108 and the port 310. The calibrant port 310 has a fluid communication path 422 extending throughout the length of the port 310.

Figure 4C:
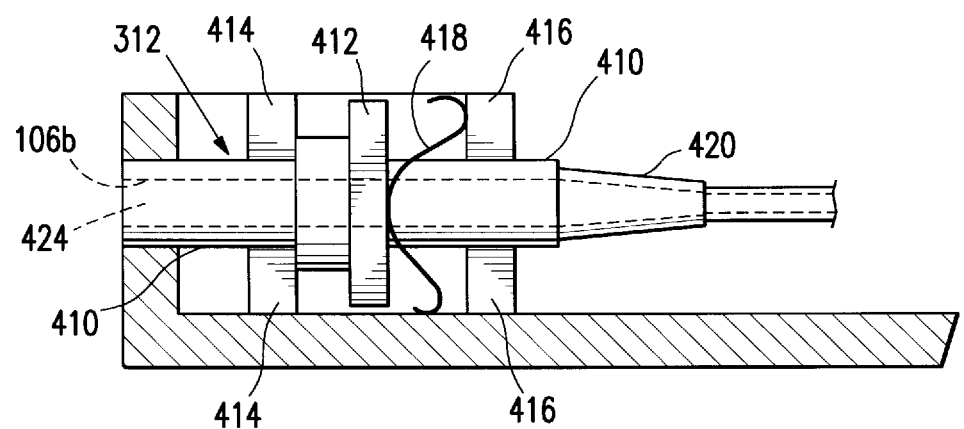

FIG. 4C is a cross-sectional view of the waste fluid communication port 312. The leaf spring 418 is held in place by the back retaining walls 416 and forces the waste port against the front retaining walls 414. The flange 412 abuts the leaf spring 418. When a fluid fitting 108 engages the waste port 312, the port assembly 312 is forced rightward (with reference to FIG. 4C), and the flange 412 is forced against the leaf spring 418. The leaf spring 418 provides compliance against the force of the fluid fitting 108, but also forces the waste port 312 leftward back against the fluid fitting 108 to ensure proper engagement of the fitting 108 and the port 312. The front retaining walls 414 retain the waste port 312 in the leftward direction. Like the calibrant port 310, the waste port 312 has a fluid communication path 424 extending throughout the length of the port 312.

FIGS. 5A–5F illustrate an exemplary embodiment of the calibrant fluid communication port 310. For convenience, the fluid communication port shown in FIGS. 5A–5F and described below will be referred to as a calibrant fluid communication port. The fluid communication port shown in FIGS. 5A–5F is not limited, however, to the calibrant bags 302, 304, but can also be used for a waste bag 306. As can be seen in FIGS. 4A–4C, however, the waste port 312 may differ from the calibrant port 310, because, preferably, the waste port 312 is coupled to the waste bag 306 by tubing 308, while the calibrant bags 302, 304 are preferably directly coupled to the calibrant ports 310 to provide substantially gas-tight seals.

Figure 5A:
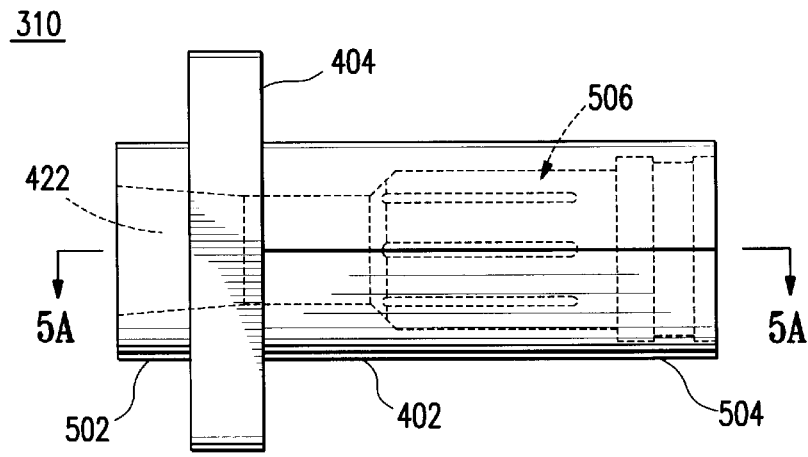
FIG. 5A is a side-view of an exemplary calibrant fluid communication port of the present invention.

FIG. 5A is a side-view of the exemplary calibrant fluid communication port 310 of the present invention. The fluid communication port 310 has a port body 402, a flange 404, a fitting end 502, a bag end 504, a fluid communication path 422, and a self-sealing valve assembly 506. The self-sealing valve assembly 506 is located within the fluid communication path 422, which is coaxial with the port body 402. The flange 404 substantially surrounds the port body 402, the two elements preferably being an integral assembly formed from polypropylene. Those skilled in the art will recognize that, while polypropylene is the preferred material, other suitable materials exist.

Figure 5B:
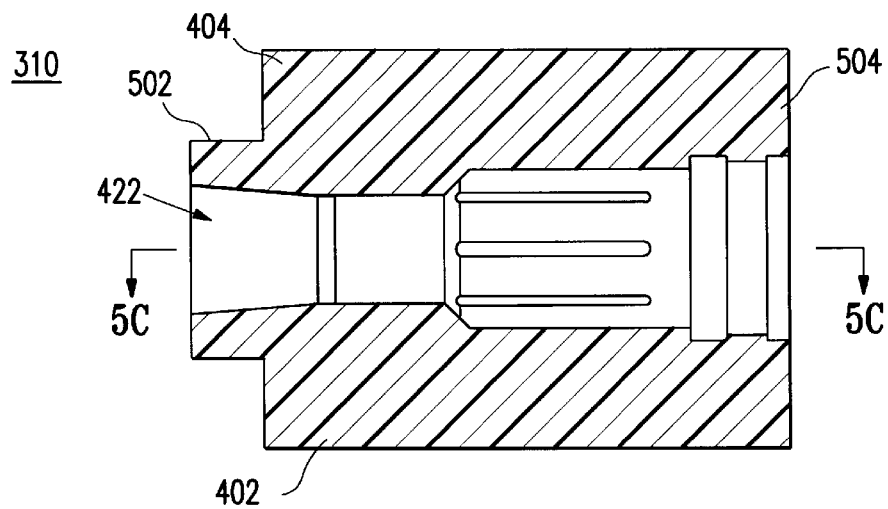
FIG. 5B is a cut-away view of the calibrant fluid port along line 5A—5A.

FIG. 5B is a cut-away view of the calibrant port 310 along line 5A—5A. The view of FIG. 5B shows that the bag end 504 is asymmetrical in shape, as it is wider in one cross section (FIG. 5B) than in the other (FIG. 5A). Preferably, if the calibrant bag 302, 304 is made from a flexible aluminum material, the bag end 504 is substantially elliptical in shape, for thermally-sealing the calibrant bag 302, 304 to the calibrant port 310. An elliptical shape facilitates a stronger thermal seal between the bag and the port. If thermally sealed, the material from which the port 310 is made should be compatible with the melting characteristics of the bag material. Alternatively, the port 310 and the bag 302, 304 can be adhesively coupled to one another. FIG. 5B also shows that, from this view, the flange 404 and the bag end 504 have the same dimensions.

Figure 5C:
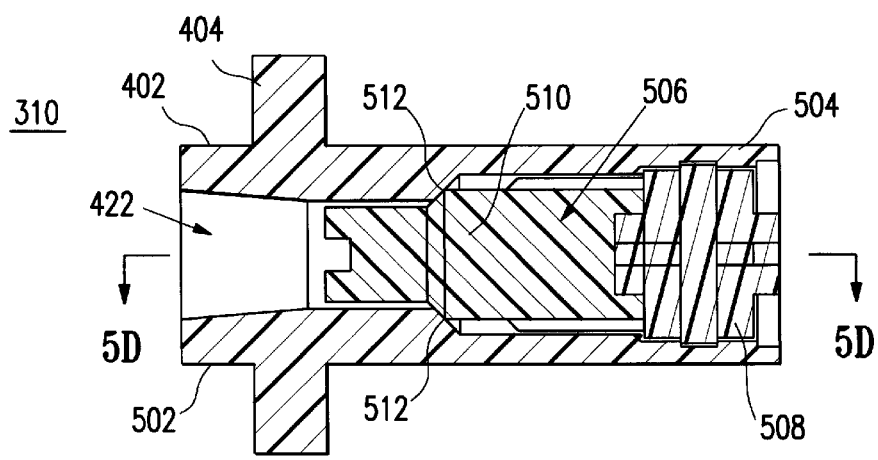
FIG. 5C is a cut-away view of the calibrant fluid port along line 5C—5C, showing a self-sealing valve assembly within the port.

FIG. 5C is a cut-away view of the calibrant port 310 along line 5C—5C showing the self-sealing valve assembly 506. The assembly is preferably a poppet valve, including a stem backstop 508 and a stem 510, the latter preferably being made of silicon. When a fluid fitting 108 (preferably a Luer fitting) is inserted into the fluid communication path 422, the fitting 108 engages the silicon stem 510 (which is compressible), forcing the stem 510 back against the stem backstop 508, which is secured in place within the fluid communication path 422 of the port body 402. The silicon stem 510 is thus pushed rightward (with reference to FIG. 5C) until a gap forms between the stem 510 and bevels 512. This creates an opening through the fluid communication path 422 to the stem backstop 508, which has channels through which fluid can flow, thereby allowing fluid flow through the calibrant port 310 and into or out of the calibrant bag 302, 304.

When the fluid fitting 108 is removed from the fluid communication path 422 of the calibrant port 310, the resilient silicon stem 510 expands leftward (with reference to FIG. 5C), resealing the gap between the stem 510 and the bevels 512, thereby preventing further fluid flow through the fluid communication path 422. Thus, in the preferred embodiment, the calibrant port 310 is self-sealing, so that, when the cartridge 104 is removed from the housing 102, no appreciable amount of fluid will flow out of the calibrant bags 302, 304. Also, it is preferred that the valve mechanism of the waste bag 306 is self-sealing to similarly prevent fluid flow into or out of the waste bag 306 when the cartridge 104 is removed from the housing 102.

Figure 5D:
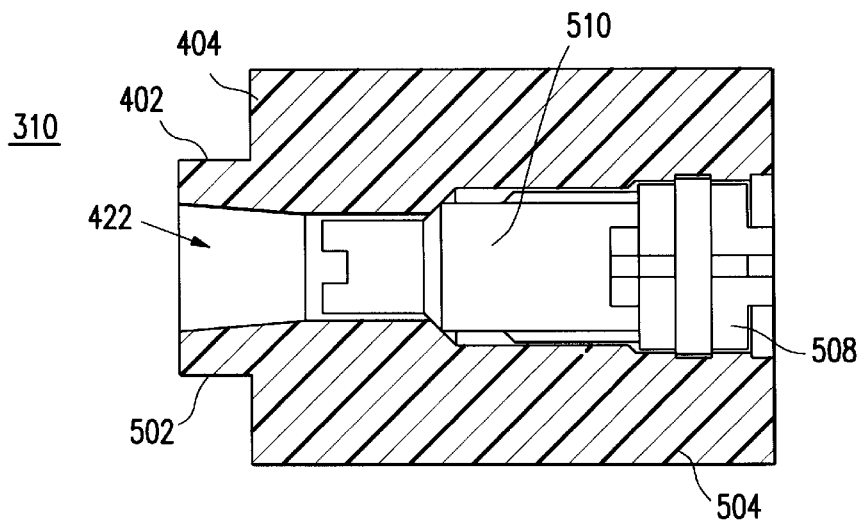
FIG. 5D is a top cut-away view of the calibrant fluid port along line 5A—5A, showing the self-sealing valve assembly and an elliptical shape on the end of the port that engages the calibrant bag.
Figure 5E:
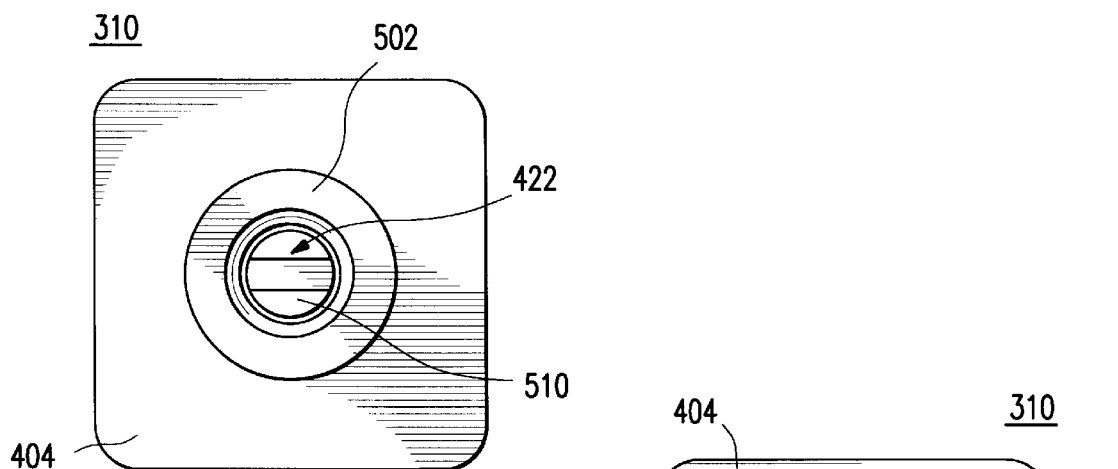
FIG. 5E is a front view of the calibrant fluid port, showing a flange on the port.
Figure 5F:
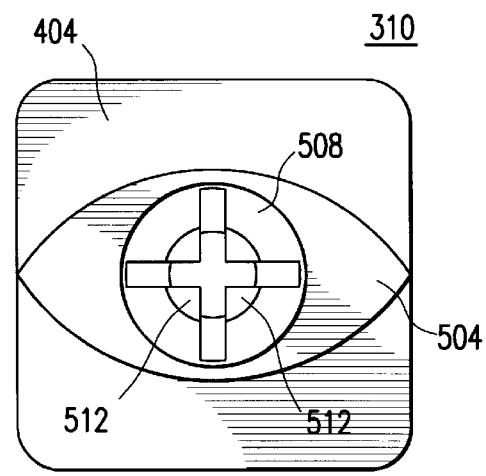
FIG. 5F is a rear view of the calibrant port.

FIG. 5D is a top cut-away view of the calibrant port 310 along line 5D—5D showing the self-sealing valve 506 with respect to the preferred elliptical bag end 504. FIG. 5E is a front view of the calibrant port 310 showing that the flange 404 is preferably rectangular in shape and showing the front of the valve stem 510 within the fluid communication path 422. FIG. 5F is a rear view of the calibrant port 310, showing the elliptical shape of the bag end 504 and the rear of the stem backstop 508 within the fluid communication path 422. As can be seen, the stem backstop 508 has spaces (or channels) 512 through which fluid can flow.

IV. Features of the Calibrant Bags

A. Over-Filling

Figure 6:
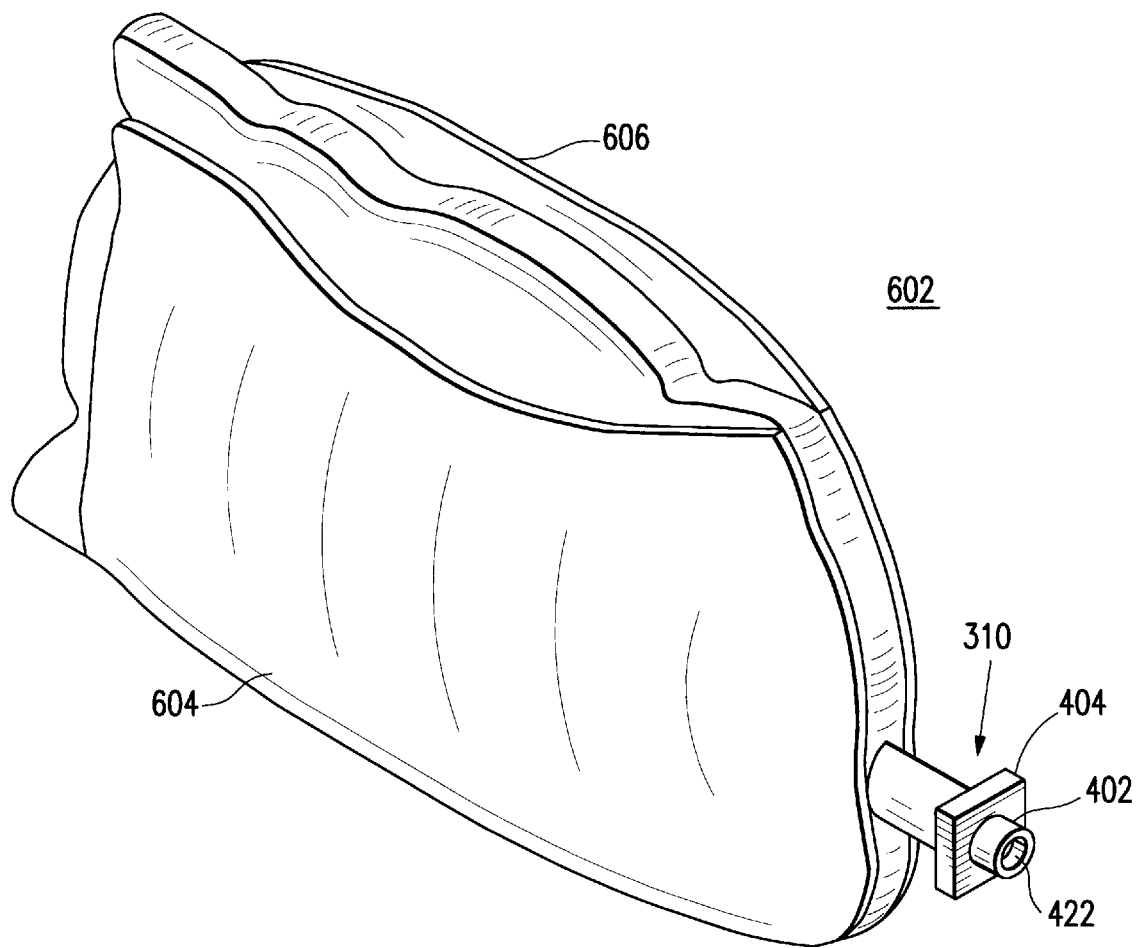
FIG. 6 shows an over-filled calibrant bag with a protective layer.

The calibrant bags 302, 304 can be made from a flexible material, preferably aluminum, and a flexible calibrant bag may be filled to an internal pressure that is greater than the ambient atmospheric pressure at sea level surrounding the flexible calibrant bag. (For convenience, a flexible calibrant bag that is filled to a relatively high internal pressure will be referred to for the remainder of this description as an "over-filled calibrant bag.") FIG. 6 shows an over-filled calibrant bag 602. In accordance with this invention, an over-filled calibrant bag 602 is defined as a calibrant bag that is filled to an internal pressure at least about 1.01 times greater than the ambient surrounding pressure at sea level.

By over-filling the calibrant bags, they can hold more calibration fluid than conventional calibrant bags, which are filled to an internal pressure equal to the ambient pressure surrounding the bag. The ability to hold more calibration fluid means the over-filled calibrant bags 602 last longer and need not be replaced as often as conventional calibrant bags. This results in more blood tests per calibrant bag. As the calibration fluid is drained from the over-filled calibrant bags 602 in order to calibrate and flush the blood analyzer 100, the calibrant bags 602 decrease in volume, thereby occupying less space within the cartridge 104. As described above, as the over-filled calibrant bags 602 contract, the waste bag 306. expands, filling the space left by the contracting calibrant bags 602.

Figure 7:
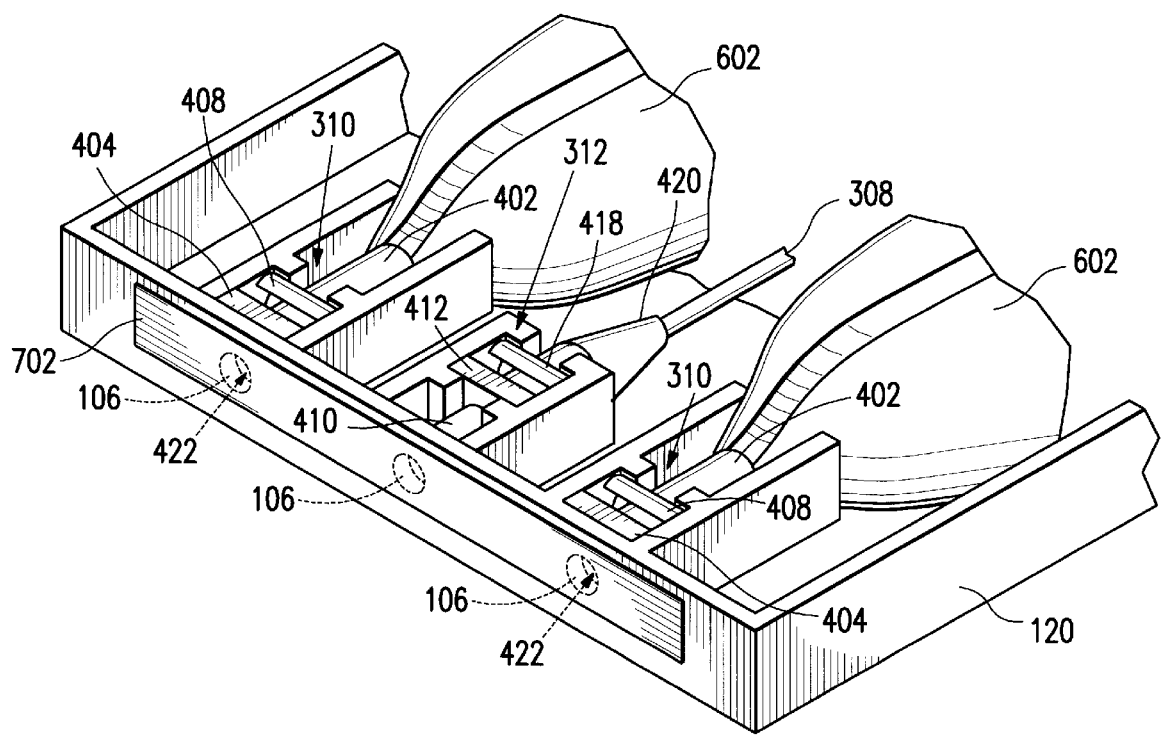
FIG. 7 shows a side of the cartridge with a foil tape covering fitting holes in the cartridge.

In the present invention, the fluid communication ports (or valve) 310 on the over-filled calibrant bag 602 may be covered with an aluminum (or foil) material to prevent the escape of $CO_2$ gas through the valve 310 during transport and storage of the calibrant bag 602. FIG. 7 shows the side tray 120 with foil tape 702 covering the fitting holes 106 as well as the calibrant fluid ports 310 and waste fluid port 312. The foil tape 702 acts to prevent the escape of gases (e.g., $CO_2$ from the over-filled calibrant bags 602) and to prevent the accumulation of dust and debris. It should be understood, however, that the foil tape 702 need not be a single piece, like that shown in FIG. 7, but instead could be independent pieces covering each port from which it is desirable to prevent the escape of gases. When the cartridge 104 is ready to be inserted into the housing 102 of the blood analyzer 100, the foil tape 702 is preferably first removed, although the cartridge 104 could be inserted into the housing 102 with the foil 702 in place, and the fluid fittings 108 could puncture the foil tape 702 when inserted into the valves 310, 312. Those skilled in the art will recognize that the foil tape 702 is merely an exemplary means by which the calibrant valves 310 can be sealed against the escape of gases and contamination by dirt. Other means include metal plugs.

With the foil tape 702 in place, the over-filled calibrant bags 602 are substantially sealed against the escape of gases through the calibrant valve 310.

It is believed that the structural relationship of the calibrant bags 602, the waste bag 306, and the cartridge 104, maintain the tonometered state of the oxygen gas and maintain the pressure level within the sealed calibrant bags 602 for substantially all of their lifetime, even when changes occur in the barometric pressure surrounding the bags 602. The over-filled calibrant bags 602, when full of calibration fluid, and the empty waste bag 306, preferably fit snugly within the cartridge 104. Thus, during transport and storage (e.g., when the cartridge 104 has not been used), the over-filled calibrant bags 602 are constrained by the walls of the cartridge 104. As the over-filled calibrant bags 602 are emptied during blood tests, the void they leave within the cartridge 104 from their decreasing internal volume is filled by the expanding waste bag 306, which holds the waste blood and waste calibration fluid from the blood-gas analyzer 100. Accordingly, the over-filled calibrant bags 602 remain constrained, now by the walls of the cartridge 104 and the expanding waste bag 306, as the calibrant bags 602 are emptied of calibration fluid.

B. Protective Layering

FIG. 6 shows that a protective layer 604, 606 can be secured to the exterior of the over-filled calibrant bags 602. Preferably, the protective layer is an adhesive-backed foam that is adhered to the calibrant bags 602 before they are filled with calibration fluid. The protective foam 602, 604 may alternatively be applied after the calibration bags 602 are filled. It is desirable to cover substantially all, but not the entirety, of the exterior of the calibrant bag 602 in order to maintain a significant amount of flexibility in the calibrant bag 602. As shown in FIG. 6, two pieces of protective foam layering 602, 604 are applied to opposite sides of the calibrant bag 602, but it should be recognized that a single piece of protective layering or patches of such layering could be applied, depending on the configuration and size of the bags 602 as well as the desired amount of protection and flexibility of the bags 602. The protective layer 604, 606 has a thickness greater than about 0.005" and is preferably even thicker for greater protection, but not so thick as to significantly reduce flexibility of the bag 602.

The protective layer is especially important for the over-filled calibrant bags 602. Because those bags are filled to a relatively high internal pressure, the calibrant bags 602 are subject to puncturing from sharp objects and to the formation of pin holes from vibration and motion. Because the over-filled calibrant bags 602 of the present invention are preferably used in a portable blood analyzer 100, the calibrant bags will be subjected to a significant amount of vibration and motion, both in transport to the facility at which the bags 602 will be used, and when the blood analyzer 100 is being moved around in the facility to perform blood tests. The protective layering 604, 606 also facilitates over-filling of the calibrant bags 602, because the layering 604, 606 provides additional structural integrity and strength to the aluminum bag 602 to reduce the change of the bag 602 bursting during filling. It should be understood, however, that the protective layering 604, 606 is not limited to over-filled bags 602, but rather can be used on any fluid bag (including a waste bag) for which it is desirable to protect the bag from puncturing and explosion.

The protective layer can alternatively be a protective vinyl (or other suitable) coating. Such a coating is preferably applied by submerging the calibrant bag 602 in the coating while it is in a liquid state. When removed, the coating then dries and forms a protective layer on the calibrant bag 602. The coating could optionally be sprayed in a liquid state onto the calibrant bag 602, after which it similarly dries, forming a protective layer.

V. Conclusion

A number of embodiments of the present invention have been described. Nevertheless, it will be understood that various modifications may be made without departing from the spirit and scope of the invention. For example, the calibrant bags can be filled with calibration fluid such that the internal pressure of the bag is greater than the ambient pressure surrounding the bag, or the calibrant bags can be filled to a pressure that is less than the ambient pressure. Further, the calibrant bags can be made from a flexible aluminum material or from some other flexible, sturdy material. In addition, the cartridge can have many different configurations, and the calibrant bags can be covered, if desired, with a protective layer. Accordingly, it is to be understood that the invention is not to be limited by the specific illustrated embodiment, but only by the scope of the appended claims.

What is claimed is:

1. A fluid communication port for a calibration bag coupled to a blood analysis device, the blood analysis device having a calibration bag locating element for coupling a calibration bag that contains a blood analysis calibration fluid to the blood analysis device, the blood analysis device also having a flow fitting, the communication port comprising:

a. a port body having a fluid communication path extending throughout the length of the port body, the port body having a fitting end for accepting the flow fitting of the blood analysis device and a bag end engaging the calibration bag that contains the blood analysis calibration fluid;

b. a self-sealing valve, located substantially within the fluid communication path, that (1) substantially prevents flow of blood analysis calibration fluid from the calibration bag and of fluid into the calibration bag unless the flow fitting is engaging the self-sealing valve and (2) substantially prevents escape of gas from the blood analysis calibration fluid in the calibration bag; and c. a flange, coupled to the port body, for securing the fluid communication port to the calibration bag locating element of the blood analysis device.

2. The fluid communication port of claim 1 wherein the flange removably secures the fluid communication port to thee calibration bag locating element.

3. The fluid commination port of claim 1 wherein the flange is a substantially rectangular flange that substantially surrounds a portion of the outside surface of the port body.

4. The fluid communication port of claim 3 wherein the flange and the port body are integral.

5. The fluid communication port of claim 1 wherein the bag end of the port body has a substantially elliptical shape.

6. The fluid communication port of claim 5 wherein the calibration bag is formed substantially from a flexible aluminum material, and the substantially elliptical shape of the bag end of the port body facilitates bonding of the flexible aluminum material to the port body.

7. The fluid communication port of claim 6 wherein the substantially elliptical bag end and the flexible aluminum calibration bag are heat sealed together.

8. The fluid communication port of claim 1 wherein the port body is made from a polyolefin material.

9. The fluid communication port of claim 1 wherein the bag end and the calibration bag are secured together by an adhesive.

10. The fluid communication port of claim 1 wherein the self-sealing valve has a valve stem and a, valve stop; wherein the fluid communication path has a sealing surface; and wherein the valve stop presses the valve stem against the sealing surface to substantially prevent fluid flow through the fluid communication path unless the flow fitting is inserted into the fluid communication path and deflects the valve stem from the sealing surface.

11. A fluid communication port for a fluid bag coupled to a fluid analysis device for analyzing bodily fluids, the fluid analysis device having a flow fitting and the fluid bag containing a calibration fluid for analysis of a bodily fluid, comprising:

a. a port body having a fluid communication path extending throughout the length of the port body, the port body having a fitting end for accepting the flow fitting of the fluid analysis device and a bag end engaging the fluid bag that contains the calibration fluid for analysis of a bodily fluid;

b. a self-sealing valve, located substantially within the fluid communication path, that (1) substantially prevents flow of the calibration fluid from the fluid bag and of fluid into the fluid bag unless the flow fitting is engaging the self-sealing valve and (2) substantially prevents escape of gas from the calibration fluid in the fluid bag; and c. an alignment flange that aligns the fluid communication port to the fluid analysis device.

12. The fluid communication port of claim 11 wherein the flange is a substantially rectangular flange that substantially surrounds a portion of the outside surface of the port body.

13. The fluid communication port of claim 11 wherein the bag end of the port body has a substantially elliptical shape.

14. The fluid communication port of claim 13 wherein the calibration bag is formed substantially from a flexible aluminum material, and the substantially elliptical shape of the bag end of the port body facilitates bonding of the flexible aluminum material to the port body.

15. The fluid communication port of claim 11 wherein the self-sealing valve has a valve stem and a valve stop; wherein the fluid communication path has a sealing surface; and wherein the valve stop presses the valve stem against the sealing surface to substantially prevent fluid flow through the fluid communication path unless the flow fitting is inserted into the fluid communication path and deflects the valve stem from the sealing surface.

16. A calibration fluid container for a blood analysis device, the blood analysis device having a fluid container locating element and a flow fitting, the calibration fluid container comprising:

a. a bag holding a blood analysis calibration fluid; and b. a fluid communication port, secured to the bag, including:

(1) a port body having a fluid communication path extending throughout the length of the port body, the port body having a fitting end for accepting the flow fitting of the blood analysis device and a bag end engaging the bag, (2) a self-sealing valve, located substantially within the fluid communication path, that (1) substantially prevents flow of the blood analysis calibration fluid out of the bag and of fluid into the bag unless the flow fitting is engaging the self-sealing valve and (2) substantially prevents escape of gas from the blood analysis calibration fluid in the bag, and (3) a flange, coupled to the port body, for securing the fluid communication port to the fluid container locating element on the blood analysis device.

17. The fluid container of claim 16 wherein the flange and the port body are integral.

18. The fluid container of claim 16 wherein the bag end of the port body has a substantially elliptical shape.

19. The fluid container of claim 18 wherein the bag is formed substantially from a flexible aluminum material, and the substantially elliptical shape of the bag end of the port body facilitates bonding of the flexible-aluminum material to the port body.

20. The fluid container of claim 19 wherein the substantially elliptical bag end and the flexible aluminum bag are heat sealed together.

21. The fluid container of claim 16 wherein the self-sealing valve has a valve stem and a valve stop; wherein the fluid communication path has a sealing surface; and wherein the valve stop presses the valve stem against the sealing surface to substantially prevent fluid flow through the fluid communication path unless the flow fitting is inserted into the fluid communication path and deflects the valve stem from the sealing surface.

* * * * *